US009877886B2

(12) United States Patent
Bernardoni et al.

(10) Patent No.: US 9,877,886 B2
(45) Date of Patent: Jan. 30, 2018

(54) ADAPTER PLANE FOR SURGICAL TABLE, IN PARTICULAR FOR HIP REPLACEMENT SURGERY WITH ANTERIOR APPROACH

(71) Applicant: MEDACTA INTERNATIONAL S.A., Castel San Pietro (CH)

(72) Inventors: Massimiliano Bernardoni, Figino (CH); Mirko Giardiello, Castel San Pietro (CH); Alberto Siccardi, Sonvico (CH); Francesco Siccardi, Sonvico (CH)

(73) Assignee: MEDACTA INTERNATIONAL SA, Castel San Pietro (CH)

( * ) Notice: Subject to any disclaimer, the term of this patent is extended or adjusted under 35 U.S.C. 154(b) by 188 days.

(21) Appl. No.: 14/428,669

(22) PCT Filed: Sep. 17, 2013

(86) PCT No.: PCT/IB2013/058608
§ 371 (c)(1),
(2) Date: Mar. 17, 2015

(87) PCT Pub. No.: WO2014/045194
PCT Pub. Date: Mar. 27, 2014

(65) Prior Publication Data
US 2015/0245971 A1 Sep. 3, 2015

(30) Foreign Application Priority Data
Sep. 18, 2012 (IT) .............................. MI2012A1546

(51) Int. Cl.
*A61G 13/12* (2006.01)
*A61G 13/00* (2006.01)
(Continued)

(52) U.S. Cl.
CPC .......... *A61G 13/123* (2013.01); *A61B 6/0407* (2013.01); *A61G 13/0036* (2013.01);
(Continued)

(58) Field of Classification Search
CPC ......... A61B 5/704; A61B 6/04; A61B 6/0407; A61B 6/0421; A61B 6/0442;
(Continued)

(56) References Cited

U.S. PATENT DOCUMENTS

| 1,576,781 A | 3/1926 | Philips |
| 3,041,121 A | 6/1962 | Comper |

(Continued)

FOREIGN PATENT DOCUMENTS

| EP | 1982680 | 7/2011 |
| JP | S5114791 | 2/1976 |

(Continued)

*Primary Examiner* — Nicholas F Polito
(74) *Attorney, Agent, or Firm* — Allen, Dyer, Doppelt, +Gilchrist, P.A.

(57) ABSTRACT

Adapter plane (1') for surgical table, comprising a main portion (2') and a secondary portion (3') which define—at the top part—a surface (4') for supporting the patient, said secondary portion (3') being arranged for supporting at least one pelvis portion of the patient, said adapter plane (1') being rigidly couplable above said surgical table with the main portion (2') overlapping the surgical table and the secondary portion (3') projecting with respect to the surgical table, at least the secondary portion (3') of said adapter plane (1') being made of radiotransparent material.

15 Claims, 12 Drawing Sheets

(51) Int. Cl.
*A61B 6/04* (2006.01)
*A61G 13/02* (2006.01)

(52) U.S. Cl.
CPC .......... *A61G 13/0081* (2016.11); *A61G 13/02* (2013.01); *A61G 13/128* (2013.01); *A61G 13/125* (2013.01); *A61G 13/1225* (2013.01); *A61G 2200/325* (2013.01); *A61G 2200/58* (2013.01); *A61G 2210/50* (2013.01)

(58) Field of Classification Search
CPC .. A61G 13/123; A61G 13/0081; A61G 13/02; A61G 13/128; A61G 13/0036; A61G 13/1225; A61G 13/125; A61G 13/122; A61G 2200/325; A61G 2200/58; A61G 2210/50
See application file for complete search history.

(56) References Cited

U.S. PATENT DOCUMENTS

| | | |
|---|---|---|
| 3,041,122 A | 6/1962 | Weickgenannt |
| 3,281,141 A | 10/1966 | Smiley |
| 3,745,996 A | 7/1973 | Rush, Sr. |
| 4,113,218 A | 9/1978 | Linder |
| 4,840,362 A * | 6/1989 | Bremer ................. A61G 13/12 5/621 |
| 5,056,535 A | 10/1991 | Bonnell |
| 5,088,706 A | 2/1992 | Jackson |
| 5,349,956 A | 9/1994 | Bonutti |
| 5,806,117 A | 9/1998 | Gotfried |
| 6,244,270 B1 | 6/2001 | Lutian et al. |
| 6,484,332 B2 | 11/2002 | Korver, II et al. |
| 7,234,180 B2 | 6/2007 | Horton et al. |
| 7,343,635 B2 | 3/2008 | Jackson |
| 7,794,467 B2 | 9/2010 | McGinley et al. |
| 7,832,401 B2 | 11/2010 | Torrie et al. |
| 7,947,006 B2 | 5/2011 | Torrie et al. |
| 8,060,960 B2 | 11/2011 | Jackson |
| 8,381,331 B2 | 2/2013 | Sharps et al. |
| 8,707,476 B2 | 4/2014 | Sharps |
| 2001/0000363 A1 | 4/2001 | Borders |
| 2002/0023298 A1 | 2/2002 | Lamb et al. |
| 2004/0133983 A1 | 7/2004 | Newkirk et al. |
| 2007/0251011 A1 | 11/2007 | Matta |
| 2007/0265635 A1 | 11/2007 | Torrie et al. |
| 2010/0122414 A1 | 5/2010 | Shah |
| 2011/0002893 A1 | 1/2011 | Culiat |
| 2011/0023893 A1 * | 2/2011 | Striggow ................ A61G 13/12 128/882 |
| 2011/0099716 A1 | 5/2011 | Jackson |
| 2011/0099720 A1 * | 5/2011 | Wyslucha .......... A61G 13/0036 5/658 |
| 2011/0107516 A1 | 5/2011 | Jackson et al. |
| 2012/0124742 A1 | 5/2012 | Soto |
| 2013/0081635 A1 * | 4/2013 | Drake ................ A61G 13/0036 128/845 |
| 2013/0219623 A1 | 8/2013 | Jackson |
| 2013/0312187 A1 | 11/2013 | Jackson |
| 2013/0312188 A1 | 11/2013 | Jackson |

FOREIGN PATENT DOCUMENTS

| | | |
|---|---|---|
| JP | 2001522649 | 11/2001 |
| WO | 0118944 | 3/2001 |
| WO | 2010099358 A1 | 9/2010 |

* cited by examiner

ADAPTER PLANE FOR SURGICAL TABLE, IN PARTICULAR FOR HIP REPLACEMENT SURGERY WITH ANTERIOR APPROACH

APPLICATION FIELD

The present invention applies to the orthopaedic surgery field, and in particular it refers to an adapter plane for surgical table.

The adapter plane can be applied in the hip replacement surgery, in particular carried out with anterior approach.

The invention also refers to a surgical table comprising the aforementioned adapter plane.

PRIOR ART

A high number of patients turns to hip replacement operations every year so as to obtain the functional recovery of the articulation, damaged by diseases such as osteoarthritis.

Operations of this type—as well as other orthopaedic surgical operations—have benefited from the rapid development of the radiographic techniques. Currently, such techniques not only allow an accurate pre-operative planning of the operation, but also a real time radioscopic display of the bone site through devices such as the fluoroscope.

However, the use of the fluoroscope or similar radiographic techniques is often hindered by the use of conventional surgical tables, in which the plane for supporting the patient is made of radiopaque material.

On the other hand, the replacement of a surgical table of the conventional type implies high costs, and it cannot be excluded that the same table can be usefully used in other surgical operations with different characteristics.

In addition it should be observed that conventional surgical tables may lead to further drawbacks when used for hip replacement operations, in particular of the anterior approach type (so-called AMIS® technique).

The aforementioned technique implies a supine decubitus position of the patient and requires the use of a positioning apparatus capable of allowing an easy handling of the lower limb.

However, conventional surgical tables are not shaped to allow the required positioning of the patient, maintaining therefore a high possibility of handling the lower limb; in addition, they do not have coupling means suitable for attaching the positioning apparatus indicated above.

Thus, the technical problem on which the present invention is based is to provide a device capable of overcoming the drawbacks of the prior art described above, and in particular capable of allowing the adaptation of a conventional table to the new surgery and radiography techniques.

SUMMARY OF THE INVENTION

The aforementioned technical problem is overcome by an adapter plane for surgical table, comprising a main portion and a secondary portion which define—at the top part—a support surface for the patient, said secondary portion being arranged for supporting at least one pelvis portion of the patient, said adapter plane being rigidly couplable above said surgical table with the main portion overlapping the surgical table and the secondary portion projecting with respect to the surgical table, at least the secondary portion of said adapter plane being made of radiotransparent material.

A man skilled in the art shall immediately observe how the adapter plane described above allows to adapt a conventional surgical table to the current radiographic requirements. For example there can be provided the application of a fluoroscope with a C-shaped arm which intersects astride of the secondary portion. The fact that this portion develops projecting with respect to the radiopaque plane of the table, allows to obtain an image of the pelvis supported thereby, or of the bone site of interest for the hip replacement operation.

The main portion and the secondary portion may both be made of radiotransparent material. Thus, this allows to obtain two portions in a single piece without uselessly complicating the production system of the adapter plane.

The radiotransparent material may for example be a carbon fibre, or any other material known in the prior art suitable for the purpose.

The secondary portion may have two sides converging towards an end point arranged along a median longitudinal axis of the adapter plane. Such sides preferably have an inclination comprised between 45° and 75° with respect to the median longitudinal axis.

When the patient is positioned on the support surface, the lower limbs thereof extend projecting beyond the two converging sides.

The inclination is ideal for allowing a support of the pelvis while simultaneously allowing a wide movement range to the articulation of the hip.

The adapter plane may have a perineal support which rises at said end point.

The perineal support advantageously allows to prevent forward movements of the pelvis when the lower limb of the patient is handled in traction.

The adapter plane may advantageously comprise a connection member for the association of an apparatus for positioning the lower limb of the patient.

The connection member, which preferably develops projecting beneath the secondary portion, may be made up of a joint on which there is hinged a proximal portion of a traction arm of the positioning apparatus.

However, such connection member preferably comprises the proximal portion of the traction arm, hinged beneath the secondary portion of the surgical table. Thus, the proximal portion may be connected through a linear joint to a distal portion of the traction arm forming part of the positioning apparatus.

This preferred embodiment allows the semplification of the operation of connecting the positioning apparatus and reducing the stress on the joint, which represents a potential point of breakage.

It should be observed that the connection member may also comprise a spacing element which connects the proximal portion to the linear joint so as to maintain the two elements misaligned. Thanks to this misalignment, it is possible to remedy the angular displacement which would otherwise be present between the distal portion of the traction arm and the leg of the patient.

The adapter plane may also comprise a plurality of belts provided for allowing a quick coupling to the surgical table.

Such belts may be advantageously mounted on slides which are slidable on lateral tracks of the adapter plane, so as to allow the variation of the coupling longitudinal position thereof.

The aforementioned technical problem is also overcome by a surgical table comprising a base plane onto which there is rigidly coupled an adapter plane of the previously described type, the main portion of the adapter plane overlapping the base plane, the secondary portion projecting with respect to the base plane.

The surgical table may further comprise a radiographic equipment (preferably a fluoroscope) with a C-shaped arm arranged astride of the secondary portion of the adapter plane.

Further characteristics and advantages shall be more evident from the detailed description of two preferred non-exclusive embodiments of the present invention provided hereinafter, with reference to the attached drawings provided by way of non-limiting example.

DETAILED DESCRIPTION

With reference to FIGS. 1-6 there are identified a surgical positioning system comprising: an adapter plane 1 according to a first embodiment of the present invention, and an apparatus 20 for positioning the lower limb of the patient 500 which can be associated thereto.

Figure 1:
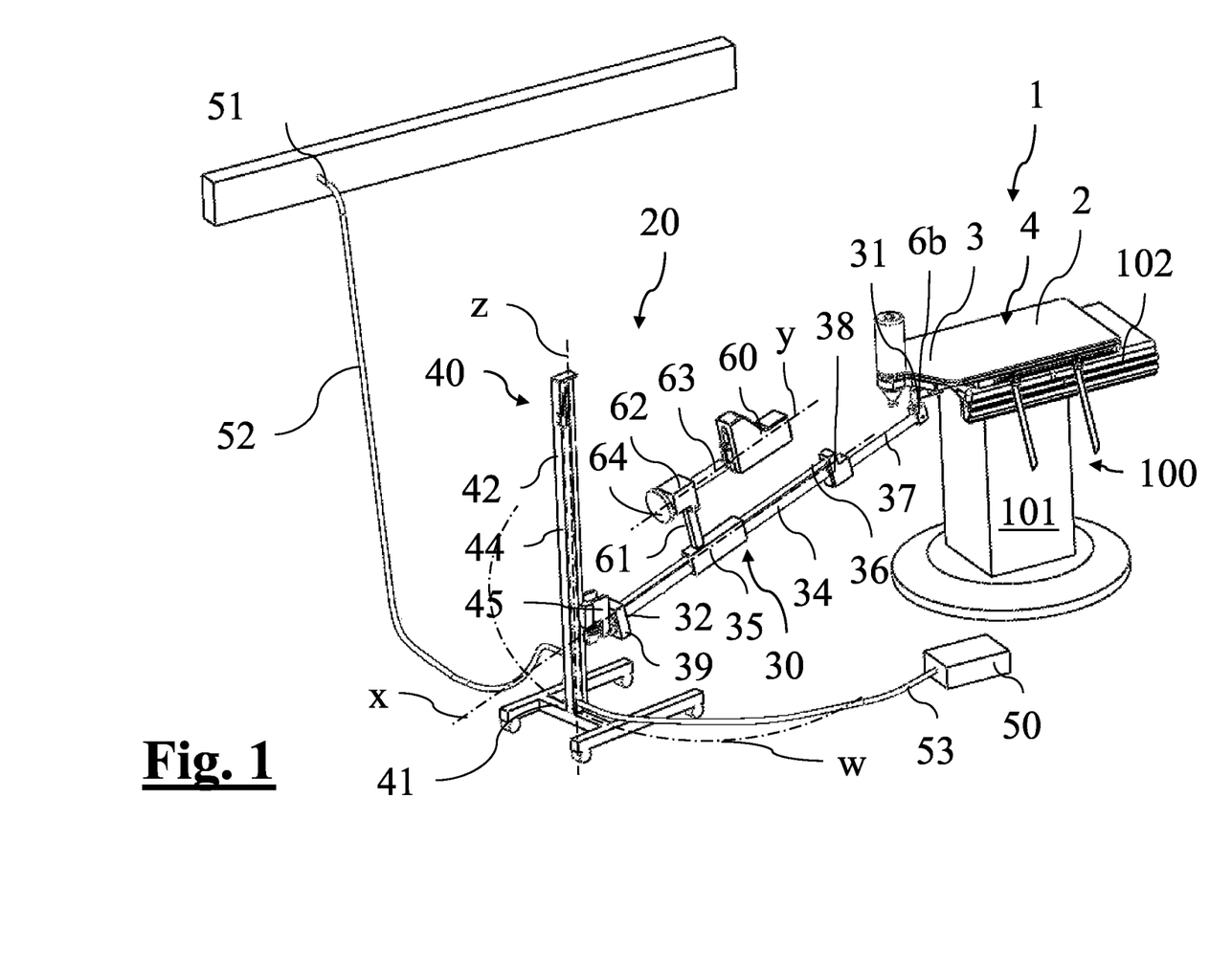
FIG. 1 represents a perspective view of a surgical table with adapter plane according to a first embodiment of the present invention, to which there is associated an apparatus for positioning the lower limb of a patient.
Figure 2:
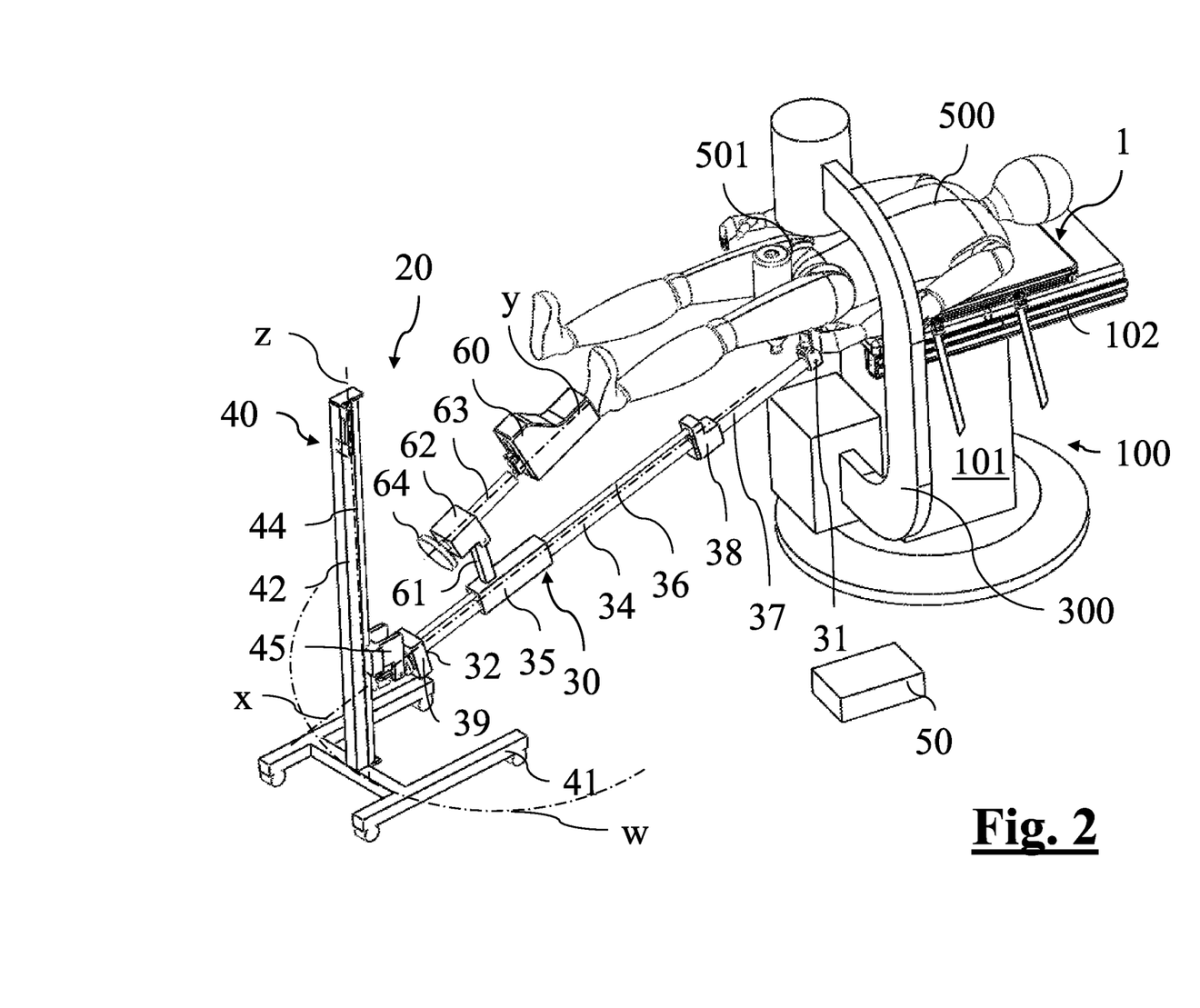
FIG. 2 represents a perspective view of the system of FIG. 1, during a hip replacement operation with anterior approach.

The adapter plane, as shown in FIGS. 1 and 2, may be rigidly coupled onto a surgical table 100. Such surgical table 100 comprises a central column 101 which hold a support plane 102, made of radiopaque material, such as for example metal material.

The adapter plane 1 comprises a main portion 2, which overlaps the support plane 102 of the surgical table. The main portion 2 has a substantially rectangular development, the width thereof is equivalent to the width of the support plane 102 partially covered thereby. Thus, the main portion 2 has two parallel sides 2a substantially aligned to the perimeter of the support plane 102 and a bottom side 2b displaced with respect to such perimeter.

The adapter plane 1 further comprises a secondary portion 3 planarly contiguous to the main one, but which extends beyond the perimeter of the underlying support plane 102. Thus, such secondary portion 3 develops projecting laterally with respect to the surgical table 100 which supports the adapter plane 1.

A radiographic apparatus 300 (preferably a fluoroscope) with a C-shaped arm, integral with the surgical table 100, is arranged astride of the secondary portion 3 of the adapter plane 1.

Figure 4:
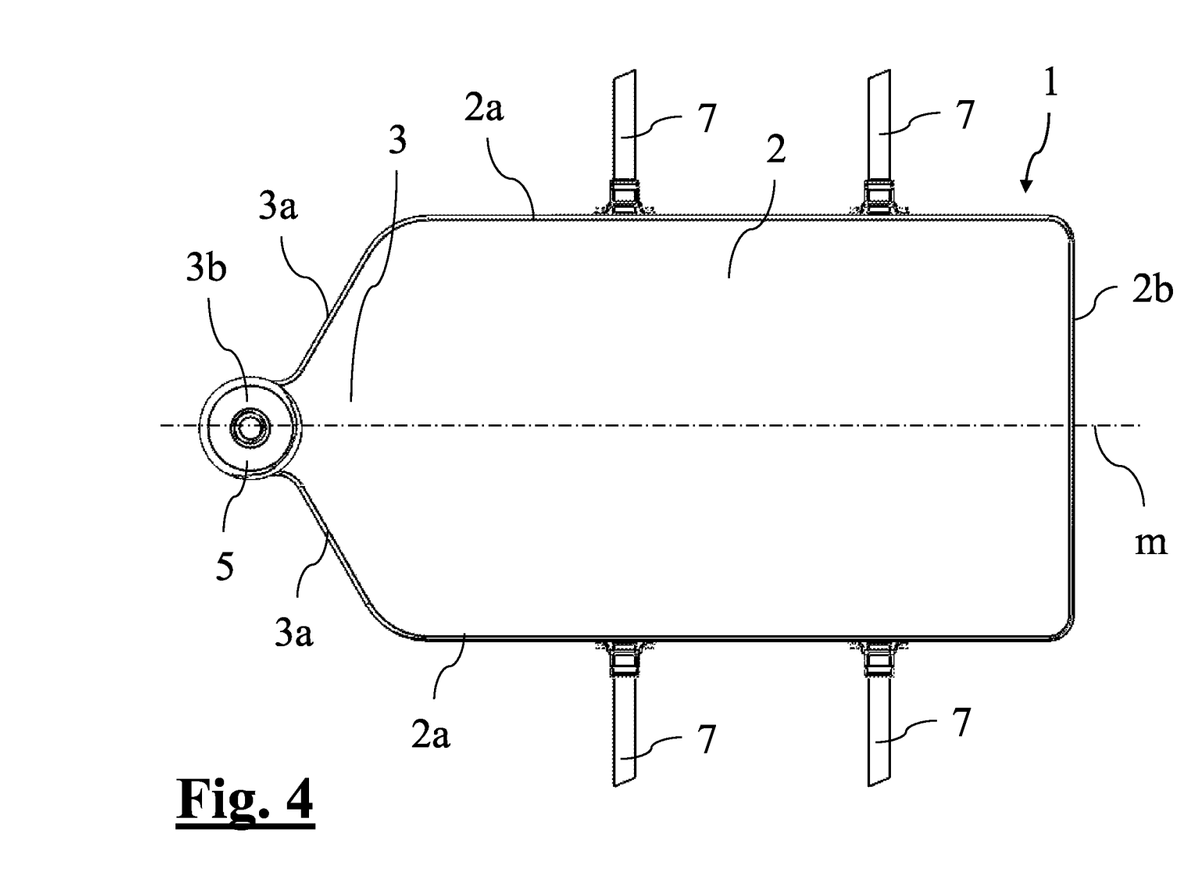
FIG. 4 represents a top orthogonal view of the adapter plane of FIG. 1.

The secondary portion 3 of the adapter plane is substantially shaped to form an isosceles triangle, i.e. it has two converging sides 3a which, starting from the parallel sides 2a of the main portion, converge towards an end point 3b arranged along a median longitudinal axis m of the adapter plane 1.

The two converging sides 3a are inclined with respect to the median longitudinal axis m by an angle comprised between 45° and 75°, in particular 60°.

Figure 5:
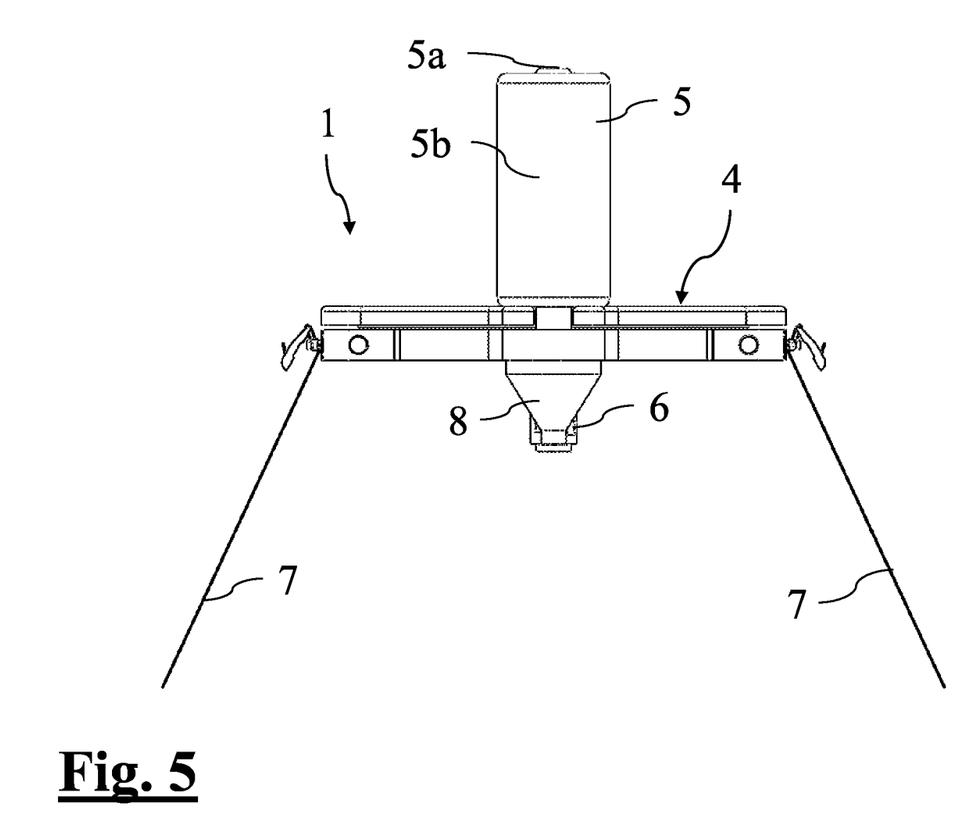
FIG. 5 represents a front orthogonal view of the adapter plane of FIG. 1.

At the end point 3b the adapter plane comprises a perineal support 5. The perineal support 5 is a vertical sleeve, which rises from the support surface 4 and is located at a front position—i.e. in further projection—with respect to the part of the plane defined by the converging sides 3a. The perineal support 5 is advantageously defined by a rigid vertical pin 5a surrounded by a padding 5b.

The lower face of the secondary portion 3 has a conical appendix 8, coaxial and opposite to the perineal support 5. The conical appendix 8 ends with an enlarged-head cylinder. Such conical appendix 8 allows the coupling of a thigh hoisting device 80, singularly observable in FIGS. 13-14, the characteristics and functions of which are described in detail hereinafter.

Figure 6:
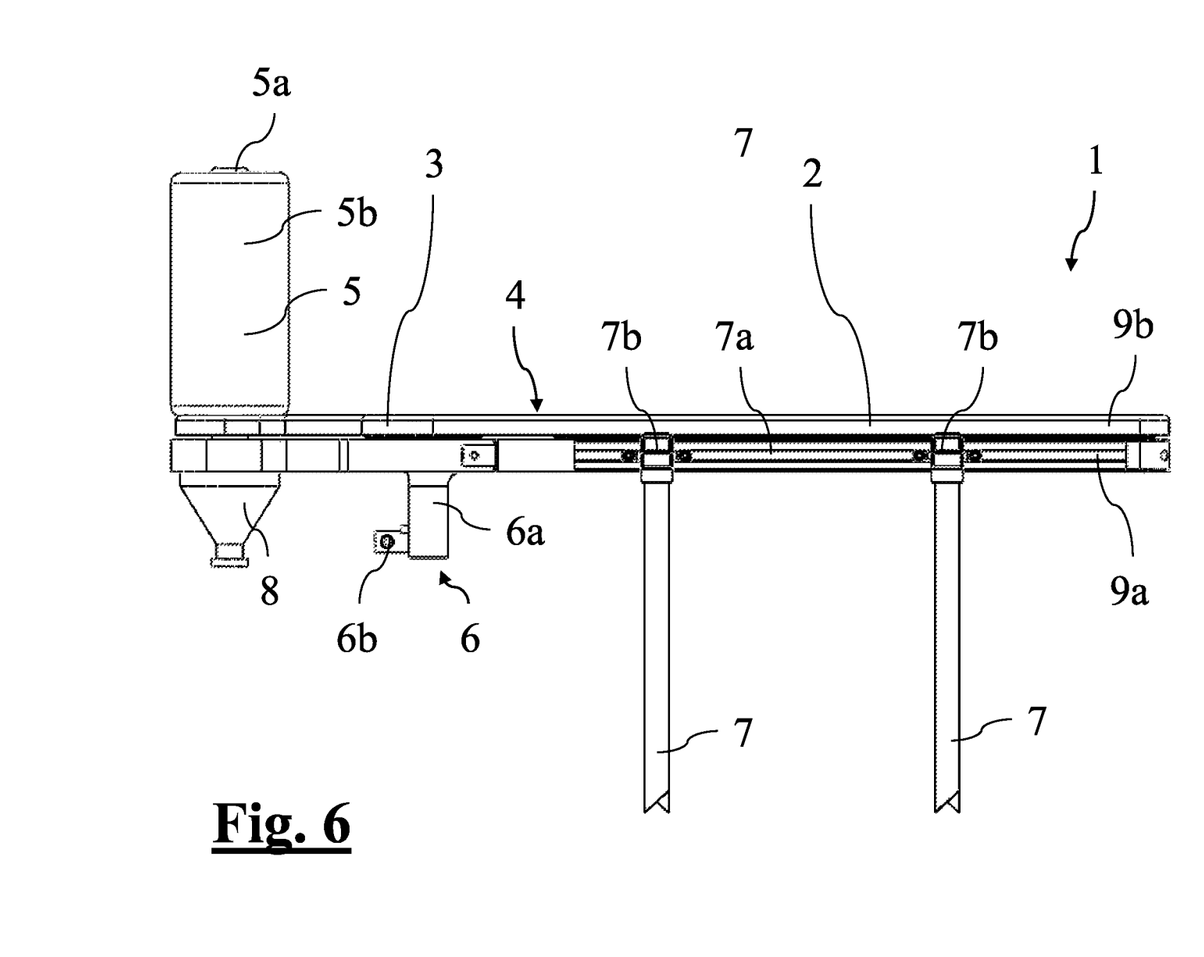
FIG. 6 represents a side orthogonal view of the adapter plane of FIG. 1.

Still on the lower face of the secondary portion 3, along the median longitudinal axis m but in a position closer to the perimeter of the support plane 102, there is extended a connection member 6 for associating the apparatus 20 for positioning the lower limb of the patient 500.

Such connection member 6 comprises a vertical appendix 6a rotatably associated below the secondary portion 3, such vertical appendix laterally bears a hinge 6b to which there can be associated a member for coupling the positioning apparatus 20.

It should be observed that the main portion 2 and the secondary portion 3 described above have a uniform structure, and they are both made of the same radiotransparent material, in particular carbon fibre.

The uniform structure of the two portions 2, 3 is divided into two functionally distinct overlapping layers; a lower layer 9a represents the actual support structure, while an upper layer 9b defines a comfort padding.

On the lower layer 9a, in particular along the parallel sides 2a of the main portion 2, there are extended two lateral tracks 7a. To each track there are associated two slidable slides 7b which carry retention means for an equivalent number of belts 7, which allow the quick fixing of the adapter plane to the underlying surgical table.

For the sake of completeness and for a better understanding of the invention, there is proposed hereinafter a summarised description of the positioning apparatus 20 which can be associated to the adapter plane 1.

The positioning apparatus 20 comprises a traction arm 30 defining a traction axis x. A proximal end 31 of such traction arm 30 is hinged to the hinge 6b of the previously described adapter plane 1. The distal end 32 is instead hinged to a framework 40 for supporting the positioning apparatus 20 as described below.

The traction arm 30 comprises a proximal portion 37, defined by a rigid bar, on the proximal end side 31; and a distal portion 34, 36, on the distal end side 32.

The distal portion 34, 36 is made up of a first actuator cylinder 34 arranged adjacent to a guide stem 36 parallel thereto; the two elements connect a proximal fitting 38, integral with the rigid bar of the proximal portion 37, to a distal fitting 39, hinged to the support framework 40.

The first actuator cylinder 34 is a double acting pneumatic cylinder of the stem-less type, i.e. internally comprising a piston not provided with a thrust stem. The internal piston is instead magnetically associated to a first slider 35, which embraces both the first actuator cylinder 34 and the guide stem 36 and it is slidable along the latter in the direction of the traction axis x. Thus, actuating the first actuation cylinder 34 it is possible to determine a stroke of the first slider 35 along the traction arm 30.

The first slider 35 carries a rigid rod 61, which extends orthogonally upwards with respect to the traction arm 30. At the end of such rigid rod 61 there is provided a connection member 62, which connects the same to a support shaft 63 at the end of which there is integrally associated a coupling 60 for the distal end of the lower limb of the patient. The coupling 60 is particularly provided in the form of a traction shoe of the known type. The connection member 62 allows to vary the angle between the rigid rod 61 and the support shaft 63.

The support shaft 63 defines a rotation axis y of the traction shoe. Within the connection member 62 there is present a rotary actuator of the pneumatic type, which allows to rotate the support shaft 63 and the traction shoe associated thereto around said rotation axis y. An emergency flywheel 64 is provided for operating the rotation, if the pneumatic system fails (for example due to power failure).

The support framework 40 is mounted on a wheel-equipped carriage 41 slidable on the floor of the operating theatre.

Such wheel-equipped carriage 41 has a horizontal H-shaped structure, from the centre of which a vertically extending upright 42 elevates according to an extension axis z.

Adjacent to the upright 42 there is arranged a second actuator cylinder 44. This cylinder is a double-acting pneumatic cylinder of the stem-less type as well, magnetically associated to a second slider 45. Thus, the second slider may be controlled sliding along the extension axis z.

The second slider 45 is hinged to the distal fitting 39 of the traction arm 30. It should be observed that there is provided a mechanical lock so as to maintain the position of the second slider 45 in case of failure of the pneumatic system (for example in case of power failure).

Furthermore, at the lower end of the support framework 40 there are provided one or more support wheels, which can be control-extracted when the second slider 45 is at a lower end-stroke position. Such support wheels allow in case of need the sliding of the wheel-equipped carriage 41 in the lateral direction. Indeed, it shall be observed that the fixed wheels of the carriage are locked in the direction of the patient, so that the carriage cannot move in the lateral direction; the support wheel is instead mounted orthogonally with respect to the others, so as to allow the lateral movement when extracted.

The positioning apparatus 20 provides for a pneumatic system which connects the first actuator cylinder 34, the second actuator cylinder 44 and the rotary actuator. The system may be suitably connected, through an inlet connection 52, to a wall-mounted socket 51 of a compressed air distribution network. The system further comprises a control unit 50, connected to the support framework 40 by means of a flexible connection 53. The control unit 50 consists of a control box provided with a pedal interface, so as to be actuated by the surgeon during the operation.

The positioning apparatus 20 allows to perform different movements on the lower limb of the patient connected thereto through the traction shoe.

By actuating the rotary actuator a rotation of the traction shoe around the rotation axis y is obtained, thus leading to an internal or external rotation of the limb.

The first actuator cylinder 34 allows to translate the traction shoe along the traction axis x, thus defining a traction of the limb or a release of such traction.

The second actuator cylinder 44 allows to lift or lower the second end 32 of the traction arm 30 along the extension axis z, respectively determining a flexure or an extension of the limb.

Lastly, after the extraction of the previously described support wheel, the wheel-equipped carriage 41 can be translated according to a circle arch w, defined by the hinging of the first end 31 of the traction arm. Such displacement defines the adduction/abduction movements of the lower limb of the patient.

Figure 3:
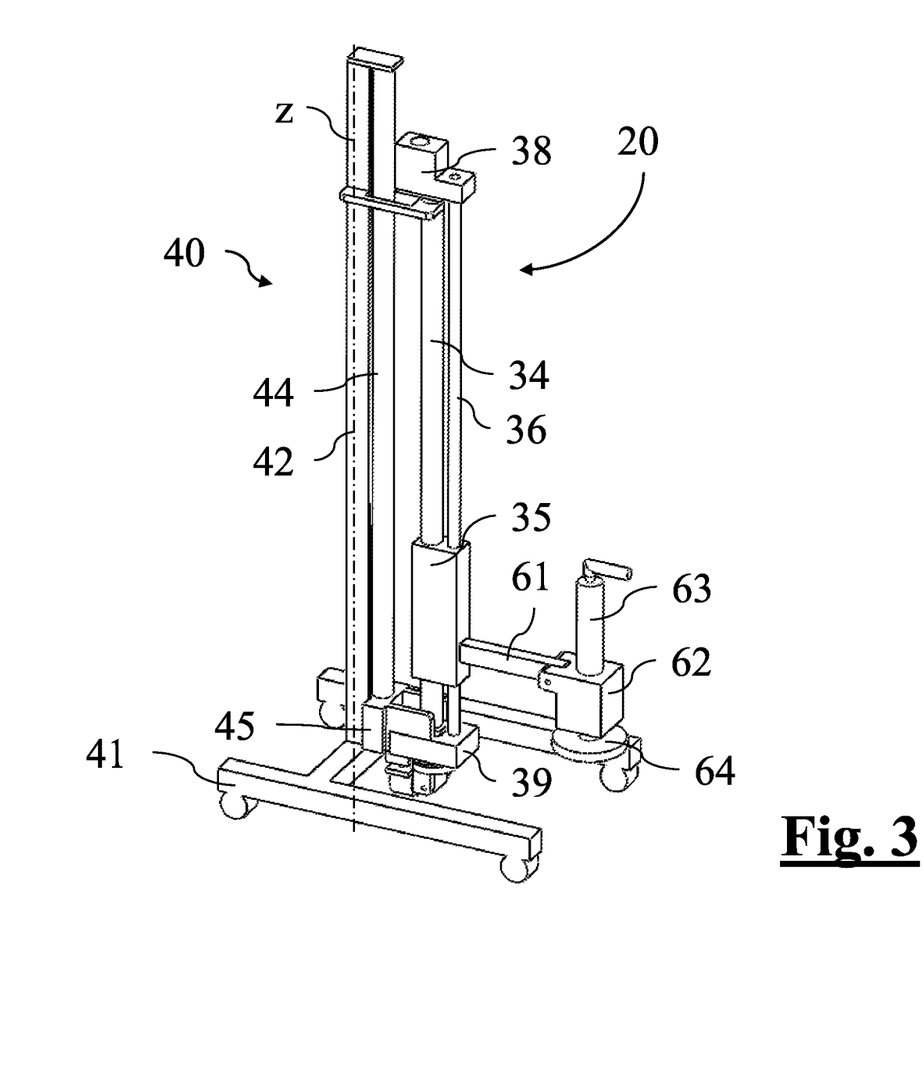
FIG. 3 represents a perspective view of the positioning apparatus visible in FIG. 1, in the folded configuration.

It should be observed that the traction arm 30 may be folded against the upright 42 of the support framework 40 with the aim of putting the apparatus away when not used, as illustrated in FIG. 3. It should be observed that in such case the rod 61 is rotated by 180° moving it outwards of the traction arm 30.

With reference to the attached FIGS. 7-12, an improved embodiment of the surgical positioning system addressed previously is identified.

Figure 7:
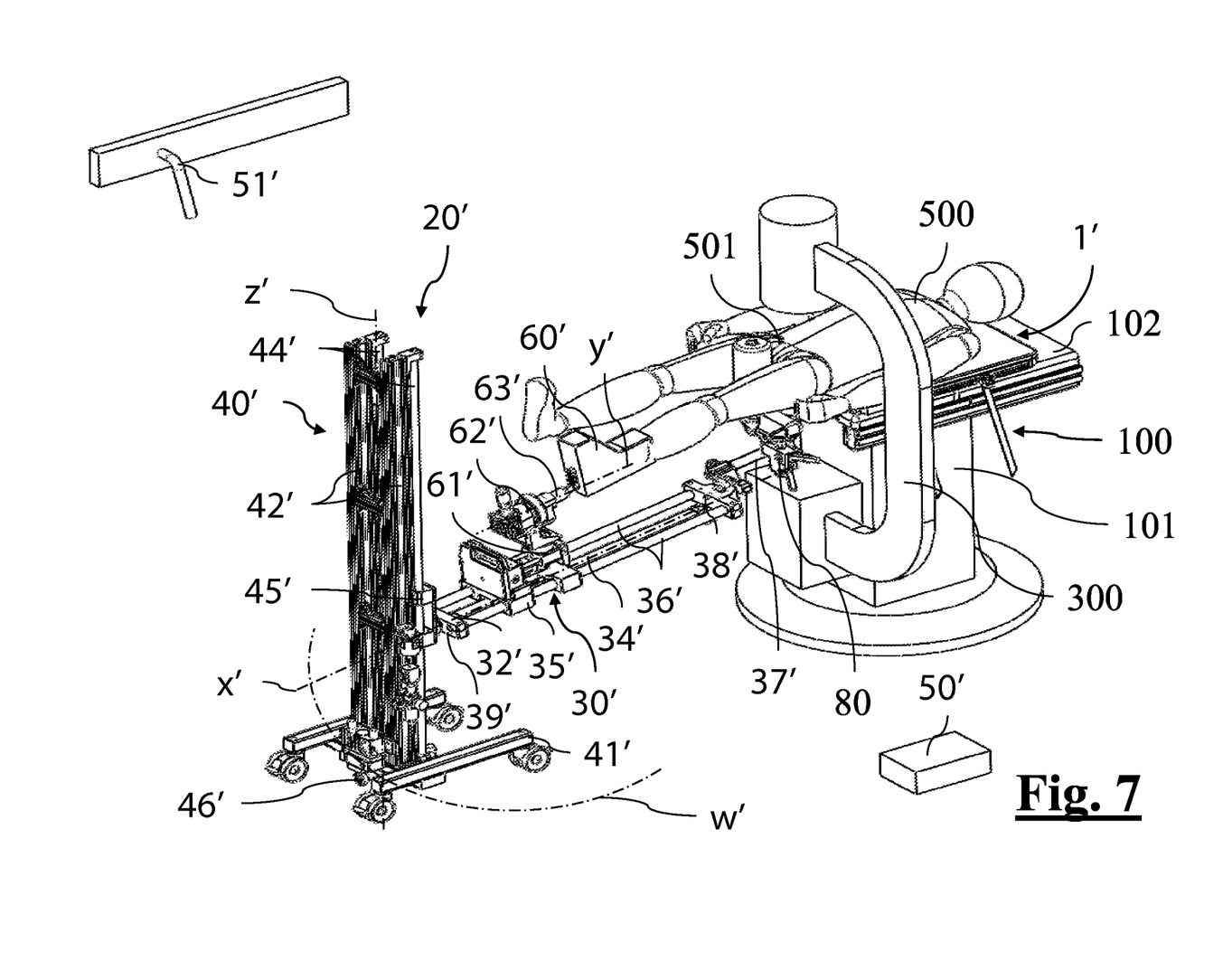
FIG. 7 represents a perspective view of a surgical table with adapter plane according to an alternative embodiment of the present invention, to which there is associated an apparatus for positioning the lower limb of a patient.

The improved surgical positioning system has a second embodiment of the adapter plane 1' according to the present invention, and an apparatus 20' for positioning the lower limb 500.

The second embodiment of the adapter plane 1' is in particular illustrated in FIGS. 9-12, where portions identical or analogous to those described previously according to the first embodiment are identified with the same reference numbers with the "first" symbol.

Figure 9:
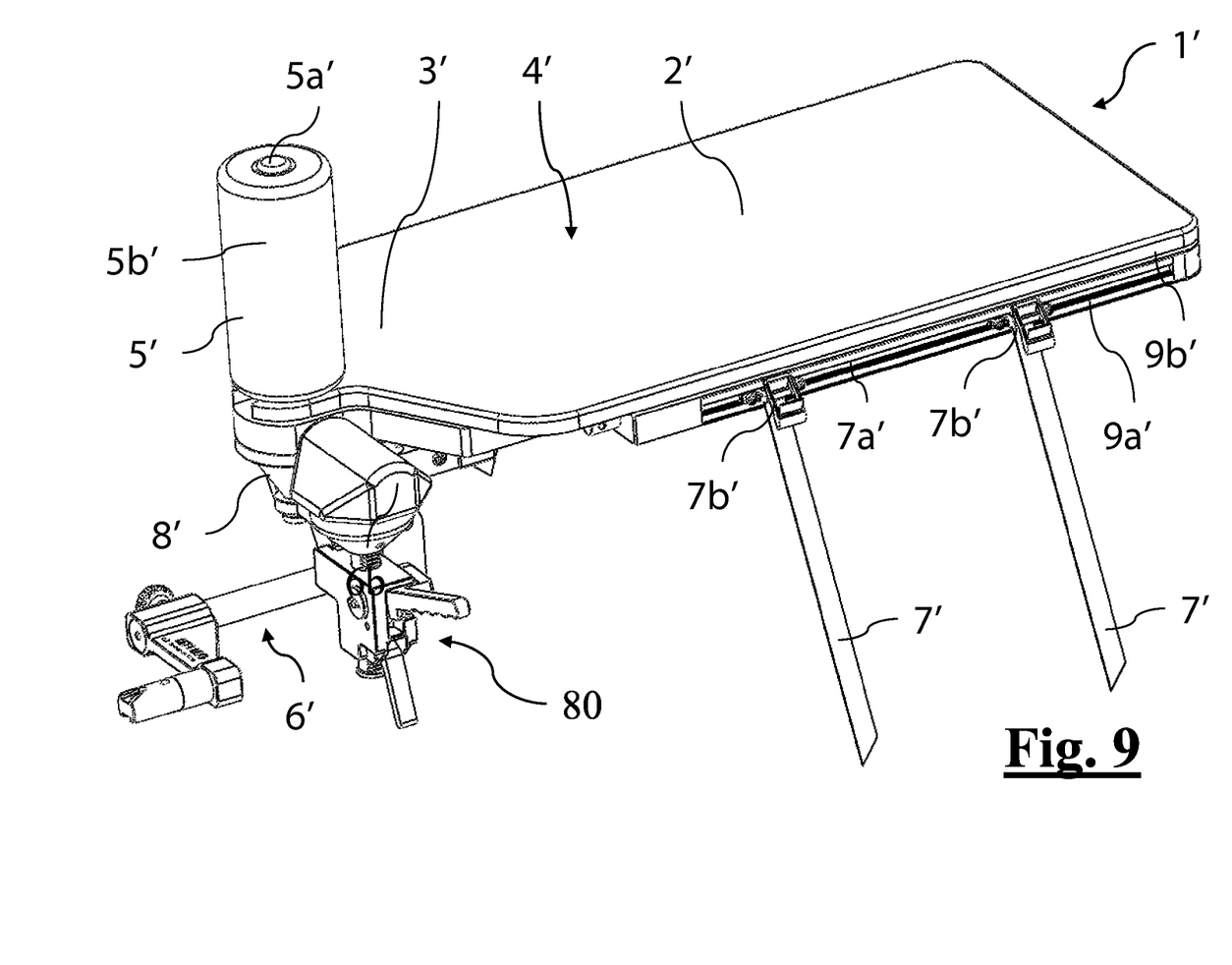
FIG. 9 represents a perspective view of the adapter plane of FIG. 7.
Figure 10:
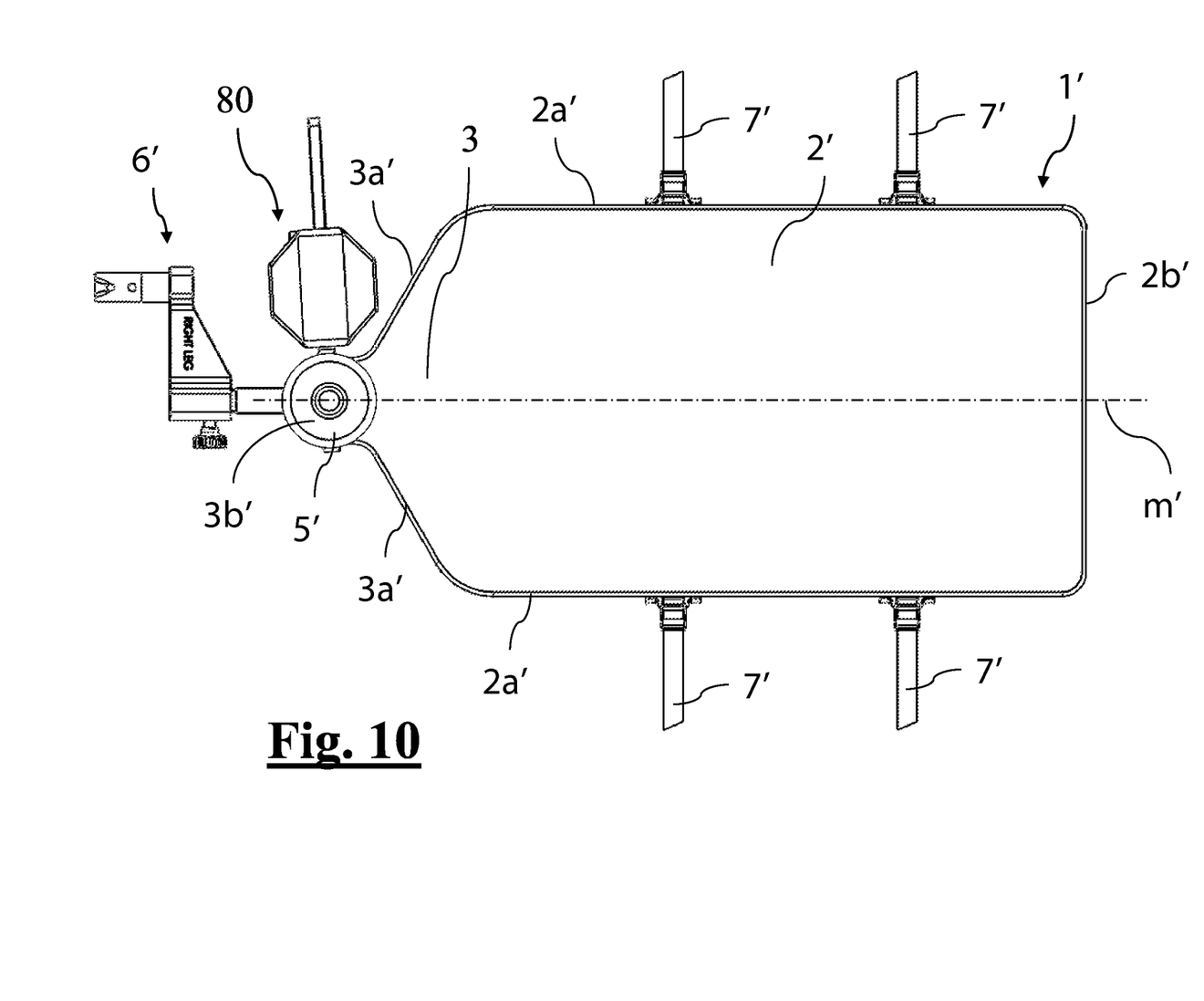
FIG. 10 represents a top view of the adapter plane of FIG. 7.

The second embodiment of the adapter plane 1' is substantially identical to the first embodiment, except for the morphology of the connection member 6' intended to be coupled with the apparatus 20' for positioning the lower limb of the patient 500.

Figure 11:
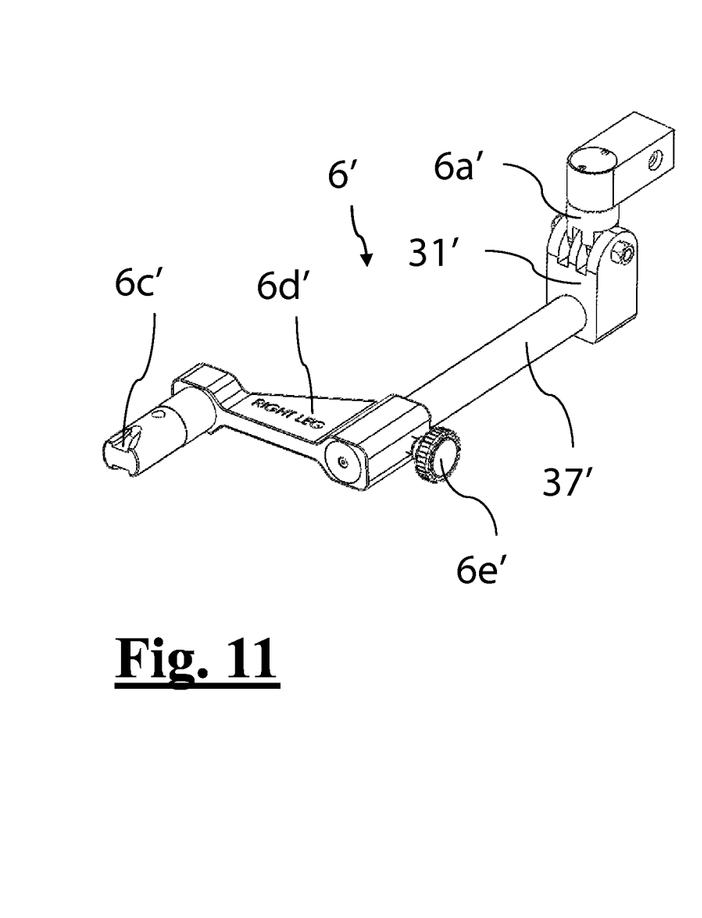
FIG. 11 represents a perspective view of a first construction detail of the adapter plane of FIG. 7, in a first configuration.
Figure 12:
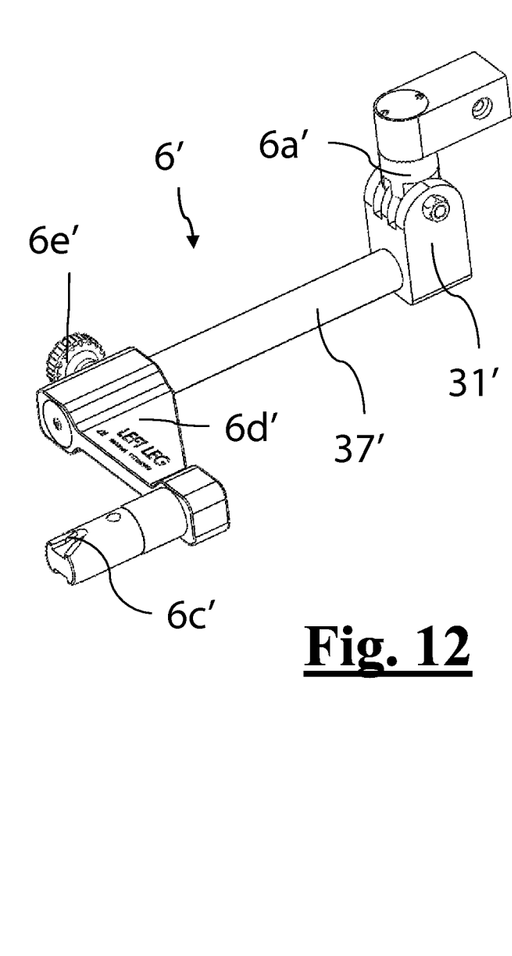
FIG. 12 represents a perspective view of the construction detail of FIG. 11, in a second configuration.

In this improved embodiment, which is illustrated in detail in FIGS. 11 and 12, the connection member 6' already comprises a proximal portion 37' of the traction arm 30'. On the contrary, the distal portion 34', 36' of such traction arm 30' remains part of the positioning apparatus, and it is connected to the previous one through a linear joint 6c'.

The connection member 6' comprises in particular a vertical appendix 6a' which extends beneath the secondary portion 3' of the adapter plane 1'. The vertical appendix 6a' is rotatably articulated with respect to the overlying plane according to a vertical axis.

Beneath the vertical appendix 6a' there is hinged, according to a horizontal axis, a proximal end 31' of the previously mentioned proximal portion 37' of the traction arm 30', which is obtained as a rigid bar.

At the distal end of the rigid bar there is associated a spacer element 6d' which connects the proximal portion 37' to the linear joint 6c'. The spacer element 6d' develops transversally with respect to the parallel axis of the proximal portion 37' and the linear joint 6c'; in particular the dimension thereof is such to allow the positioning of the linear joint 6c' beneath the lower limb of the patient 500, so as to align the traction arm 30' therewith.

It should be observed that the spacer element 6d' comprises a knob 6e' which allows to unlock the element to perform a 180° rotation around the axis of the proximal portion 37', so as to be able to adjust the configuration of the connection member 6' according to the limb to be operated.

The entire connection member 6' described above is preferably made of radiotransparent material.

The connection member 6' shows in the improved embodiment thereof several advantages with respect to the connection member 6 of the first embodiment described previously.

Firstly, the connection to the positioning apparatus is performed through a linear joint, and no longer at the point of articulation of the traction arm. This allows to simplify the operations of connecting the positioning apparatus and to reduce the stress on the joint, a potential breakage point.

Furthermore, the spacing element allows a misalignment of the two portions of the traction arm, thus allowing a perfect alignment of the distal portion with the lower limb of the patient and considerably improving the precision of the manipulations carried out through the positioning apparatus.

Lastly, the structural division of the device below the spacer element allows the entire portion of the device located within the field of action of the fluoroscope during the surgical intervention to be made of radiotransparent material.

For the sake of completeness and for a better understanding of the invention, there is proposed hereinafter a summarised description of the positioning apparatus 20' in the second embodiment of the invention.

Figure 8:
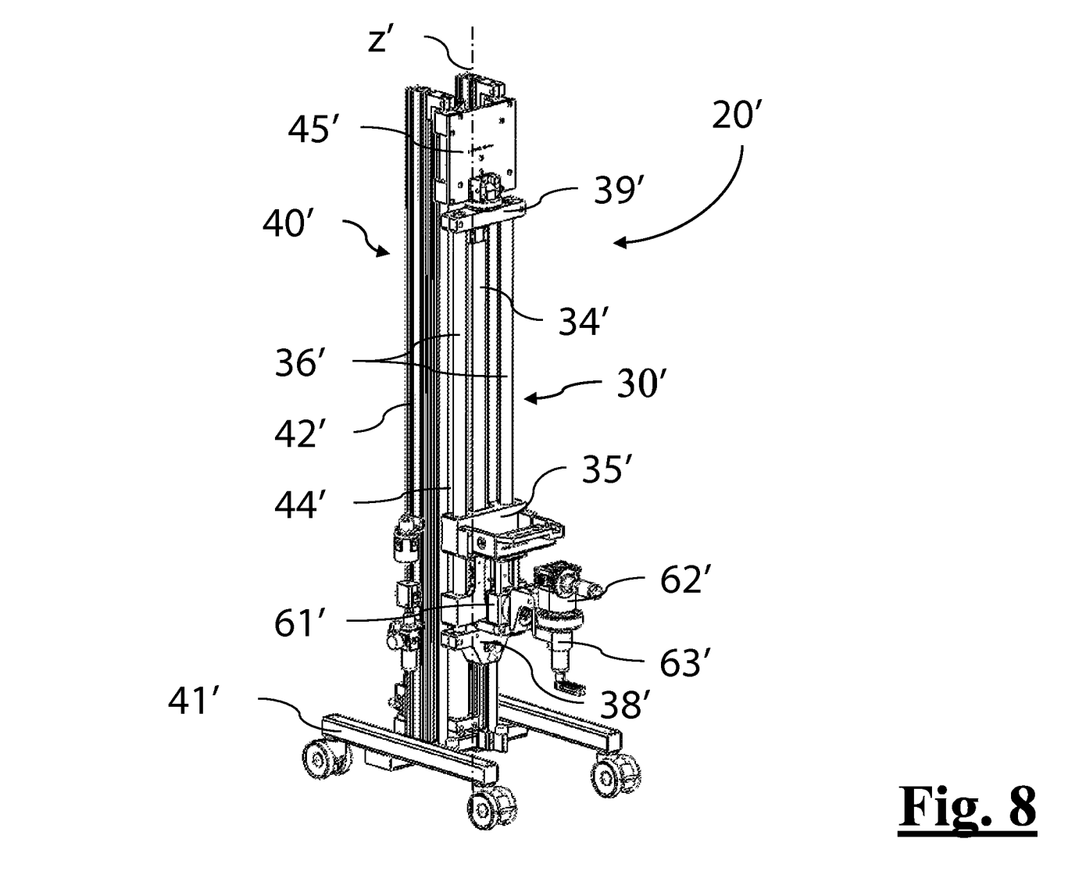
FIG. 8 represents a perspective view of the positioning apparatus shown in FIG. 7, in folded configuration.

The second embodiment of the positioning apparatus 20' is in particular illustrated in FIGS. 7 and 8, where portions identical or analogous to those described previously regarding the first embodiment are identified by the same reference numbers with the "first" symbol.

Once again, reference shall be made to the previous description for the description of the parts of the device substantially analogous to the first embodiment, while the description that follows only identifies the different aspects of the second embodiment.

Firstly, it should be observed that the traction arm 30' is now partially defined by the connection member 6' of the adapter plane 1', while the distal portion 34', 36' alone is part of the positioning apparatus 20'. In particular, it is this distal portion 34', 36', misaligned with respect to the proximal portion 37', that defines the traction axis x' parallel to the lower limb of the patient 500.

The distal portion 34', 36' itself has a different structure: it comprises two parallel guide stems 36' which connect the distal fitting 39' to the proximal fitting 38'; the latter is arranged for engaging with the previously mentioned linear joint 6c'.

The first actuator cylinder 34', still constituted by a double acting pneumatic cylinder of the stem-less type, is arranged between the two guide stems 36', in a slightly lowered position with respect thereto.

The first slider 35' embraces both guide stems 36' and the first actuator cylinder 34' interposed thereto.

The first slider 35' no longer has a rigid rod, which has been replaced by an adjustable slide 61' according to the traction axis x' over which there is provided an adjustable connection member 62', provided with as before of support shaft 63' and the relative shoe coupling 60'.

The structure of the support framework 40' is substantially analogous to that of the previously described embodiment, excluding the doubling of the upright/actuator assembly 42', 44' so as to confer greater mechanical resistance to the entirety.

Furthermore, it should be noted that in FIG. 7 there can be observed a concealable support wheel 46' which allows the lateral movement of the support framework 40'; the representation of such element was omitted in the drawings regarding the first embodiment for the sake of clarity.

Furthermore, it should be observed that the pneumatic system of the second embodiment is substantially analogous to that of the first embodiment; the connections of the wall socket 51' and of the control unit 50' to the support framework 40' were omitted in FIG. 7 for the sake of clarity.

Lastly, it should be noted that, with reference to the second embodiment described previously, the folding position provides for the positioning of the second slider 45' in an upper end-stroke position and the consequent folding of the traction arm 30' downwards along the column of the support framework 40'. Such folding mode, represented in FIG. 8, does not provide for the 180° rotation of the connection member 62'.

Lastly, there is described the thigh hoisting device 80, couplable to the conical appendix 8; 8' of the adapter plane 1; 1' in both embodiments thereof.

Figure 13:
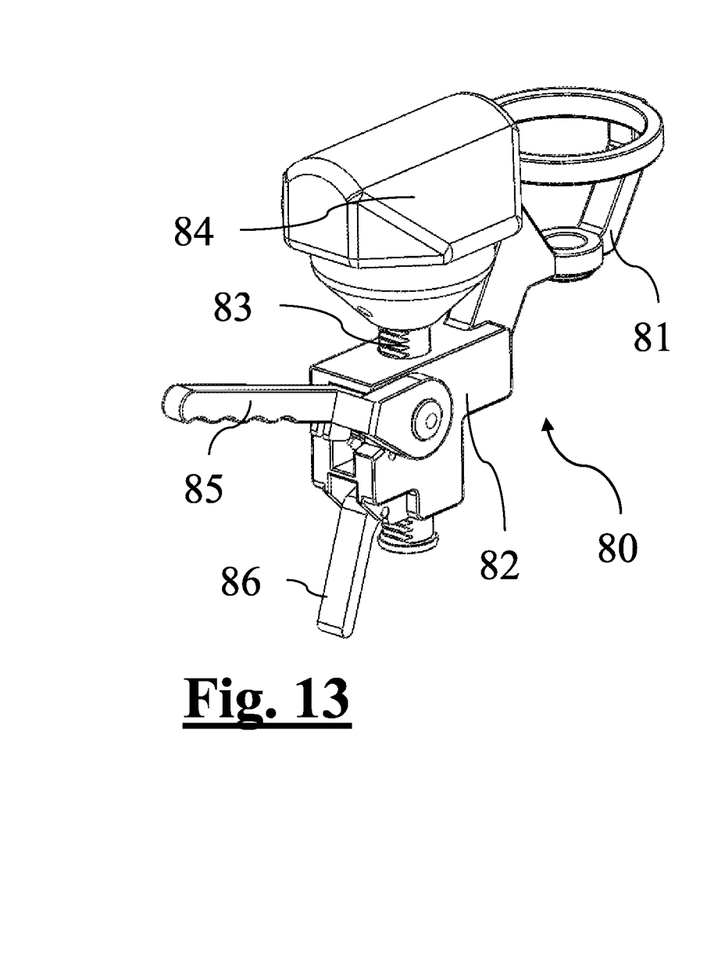
FIG. 13 represents a perspective view of a second construction detail of the adapter plane of FIG. 7.
Figure 14:
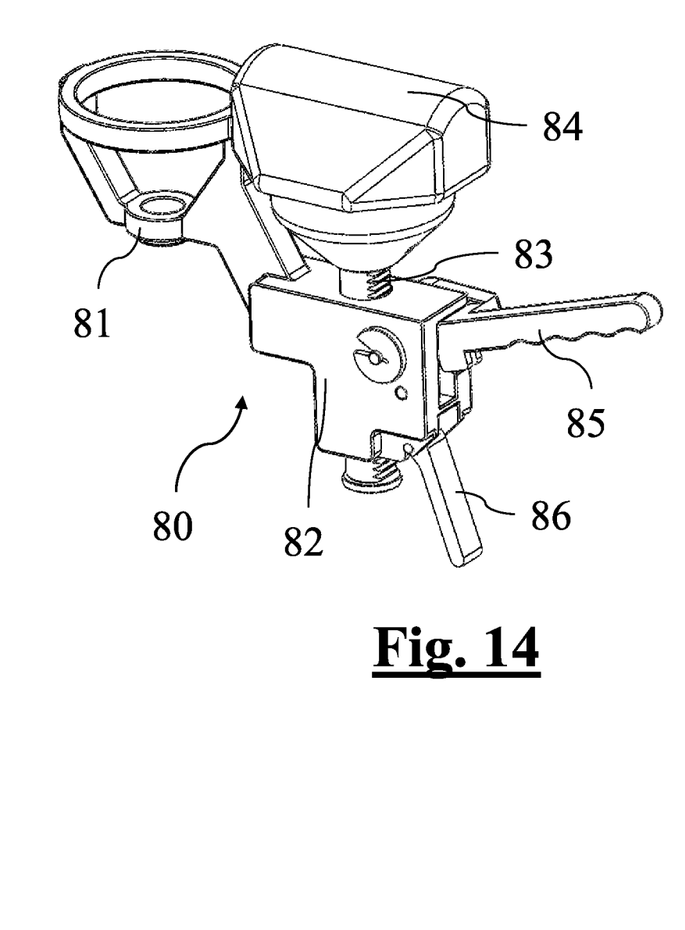
FIG. 14 represents another perspective view of the second construction detail of FIG. 13.

The thigh hoister 80, singularly observable in FIGS. 13-14, comprises a main body 82 from which a cup-like coupling appendix 81 departs couplable to the conical appendix 8, 8'. The defined coupling is of the rotatable type, so that the thigh hoister 80 can be easily moved rightwards or leftwards with respect to the end 3b, 3b' depending on the limb to be operated.

The main body 82 houses a vertically movable rack rod 83, which carries—at the top part—a cushion 84 for supporting the thigh of the patient.

The thigh hoister 80 provides for an actuation lever 85, which cooperates with the rack rod 83 thus determining a predefined hoisting of the support cushion 84 upon each traction. The movement of the rack rod 83 in the opposite direction is prevented by a proper hook integral with the end of a release lever 86; when the release lever 86 is actuated, the hook no longer exerts its locking action and the support cushion 84 lowers due to gravity.

The thigh hoister is made of plastic material or in any case radiotransparent material so as to not interfere with the operation of the fluoroscope.

Obviously, various modifications and variants to the described invention may be implemented by a man skilled in the art with the aim of meeting contingent and specific requirements, each of said modifications and variants falling within the scope of protection of the invention as defined by the following claims.

The invention claimed is:

1. An adapter plane for a surgical table and for supporting a patient, the adapter plane comprising:
   a distal support portion; and
   a proximal support portion extending from and being coupled to said distal support portion and being adjacent a device for positioning a lower limb of the patient;
   said distal support portion to be placed over said surgical table;
   said proximal support portion to support at least a pelvis of the patient;
   said distal support portion to support a back of the patient, the proximal support portion extending outwardly from the surgical table;

said proximal support portion comprising radio frequency (RF) transparent material;

said proximal support portion having a proximal end, and first and second opposing sides converging at said proximal end, said proximal end being aligned with a longitudinal axis of said adapter plane;

said proximal end to be coupled to the device for positioning the lower limb of the patient and comprising a first appendix arm extending from and transverse to said proximal support portion and configured to rotate, a hinge extending from said first appendix arm and to be coupled to a member for coupling the device for positioning the lower limb of the patient, and a second appendix arm extending from and transverse to said proximal support portion and for coupling to a thigh hoisting device, the second appendix arm being cone-shaped.

2. The adapter plane according to claim 1, wherein said distal support portion and said proximal support portion are both made of RF transparent material.

3. The adapter plane according to claim 1, wherein said RF transparent material comprises is carbon fiber.

4. The adapter plane according to claim 1, wherein said first and second opposing sides have a cant between 45° and 75° with respect to the longitudinal axis of said adapter plane.

5. The adapter plane according to claim 1, further comprising a perineal support elevating adjacent said proximal end.

6. The adapter plane according to claim 1, wherein the member comprises a proximal portion of the device for positioning the lower limb of the patient, hinged below the proximal portion of the surgical table and connectable through a linear joint to a distal portion of the device for positioning the lower limb of the patient.

7. The adapter plane according to claim 1, further comprising a plurality of belts configured to allow coupling to the surgical table.

8. The adapter plane according to claim 1, wherein the thigh hoisting device is at the proximal portion.

9. A surgical table comprising;

a base plane; and an adapter plane coupled to said base plane for supporting a patient, said adapter plane comprising a distal support portion; and a proximal support portion extending from and being coupled to said distal support portion and being adjacent a device for positioning a lower limb of the patient;

said distal support portion to be placed over said base plane;

said proximal support portion to support at least a pelvis of the patient;

said distal support portion to support a back of the patient, the proximal support portion extending outwardly from said base plane;

said proximal support portion comprising radio frequency (RF) transparent material;

said proximal support portion having a proximal end, and first and second opposing sides converging at said proximal end, said proximal end being aligned with a longitudinal axis of said adapter plane;

said proximal end to be coupled to the device for positioning the lower limb of the patient and comprising a first appendix arm extending from and transverse to said proximal support portion and configured to rotate, a hinge extending from said first appendix arm and to be coupled to a member for coupling the device for positioning the lower limb of the patient, and a second appendix arm extending from and transverse to said proximal support portion and for coupling to a thigh hoisting device, the second appendix arm being cone-shaped.

10. The surgical table according to claim 9, wherein said distal support portion and said proximal support portion are both made of RF transparent material.

11. The surgical table according to claim 9, wherein said RF transparent material comprises carbon fiber.

12. The surgical table according to claim 9, wherein said first and second opposing sides have a cant between 45° and 75° with respect to the longitudinal axis of said adapter plane.

13. The surgical table according to claim 9, wherein said adapter plane further comprises a perineal support elevating adjacent said proximal end.

14. The surgical table according to claim 9, wherein said adapter plane further comprises a plurality of belts configured to allow coupling to the surgical table.

15. The adapter plane according to claim 9, wherein the thigh hoisting device is at the proximal portion.

* * * * *